(12) United States Patent
Nösel et al.

(10) Patent No.: US 6,439,541 B1
(45) Date of Patent: Aug. 27, 2002

(54) TROCAR SLEEVE WITH A DUCKBILL VALVE

(75) Inventors: Bernd Nösel, Lütjensee; Michael Wiegand, Glinde, both of (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 09/578,943

(22) Filed: May 25, 2000

(30) Foreign Application Priority Data

Jun. 2, 1999 (DE) .......................................... 199 25 324

(51) Int. Cl.[7] .............................................. A16L 29/00
(52) U.S. Cl. ................................................. 251/149.1
(58) Field of Search ....................... 264/164.01, 167.01, 264/167.03, 167.04; 251/149.1; 604/249, 256

(56) References Cited

U.S. PATENT DOCUMENTS

| | | |
|---|---|---|
| 5,301,707 A | 4/1994 | Hofsteenge |
| 5,599,305 A | 2/1997 | Hermann et al. |
| 5,727,770 A * | 3/1998 | Dennis |
| 5,827,228 A * | 10/1998 | Rowe |

FOREIGN PATENT DOCUMENTS

DE   1 226 241   10/1996

\* cited by examiner

*Primary Examiner*—Michael J. Hayes
*Assistant Examiner*—Michelle A Lewis
(74) *Attorney, Agent, or Firm*—Rankin, Hill, Porter & Clark LLP

(57) ABSTRACT

A trocar sleeve for introducing instruments into gas filled body spaces including an insertion tube and a valve chamber disposed proximally on it with a duckbill valve of elastic material. The duck bill value has a tubular body extending coaxially with respect to the axis of the insertion tube. An end of the body directed towards the insertion tube has two flat oblique walls forming a ridge with a slit extending therein transverse to the axis of the tube. The tubular body is oversized in a direction transverse to the slit with respect to the internal size of the valve chamber in the uninstalled rest state.

3 Claims, 1 Drawing Sheet

TROCAR SLEEVE WITH A DUCKBILL VALVE

BACKGROUND OF THE INVENTION

When a surgeon operates endoscopically in gas filled body spaces, he needs trocar sleeves with a gas seal to introduce the instruments in order to prevent the gas from escaping. The most common field of application is laparoscopy, that is to say working in the stomach space expanded with pressurized gas. One or more gas sealed trocar sleeves are positioned through the stomach wall and provide the necessary access for various instruments, such as optical systems, forceps, cutters and the like which are constructed with the necessary length.

A wide variety of constructions are known for sealing the trocar sleeves to prevent the escape of gas. The known seals are generally constructed in the form of non-return flap valves which are opened by the instrument when it is introduced and automatically close when the instrument is withdrawn. The Duckbill valves are constructionally particularly simple and these close the slit with their oblique walls under a pressure load from the insertion tube, which slit, however, when an instrument is inserted, is easily opened from the exterior. In addition to this non-return flap valve, elastic apertured diaphragms are generally also provided on the external openings of the valve chambers. Such diaphragms elastically surround the shaft of the instrument and are responsible for the seal when the instrument is inserted and the valve is thus open. The prior art shows such constructions of the type referred to above, e.g. in EP0652730 B1 and U.S. Pat. No. 5,141,498, with a special construction with transverse slits. However, duckbill valves have the disadvantage, like most flap valves, that they do not close cleanly when there is a very low pressure in the body space. Thus if for example the stomach space is gradually pressurised by the injection of gas, gas can still escape through the duckbill valve which can prevent the build up of pressure in the stomach space.

SUMMARY OF THE INVENTION

It is the object of the present invention to provide a trocar sleeve of the type referred to above which closes cleanly even at a low pressure differential.

If the duckbill valve is oversized in the direction transverse to the slit with respect to the internal size of the valve chamber, in the uninstalled rest state, it will be compressed transverse to the slit when instaled in the valve chamber. The elastic material of the duckbill valve then exerts a closing biasing force on the slit which holds the valve closed, even at a very low pressure differential. The valve will stay closed without the pressure forces on the oblique surfaces acting to close the slit. A trocar sleeve in accordance with the invention, can thus form a seal, during a pressure build up, even to the lowest pressures, so that the pressure build up in the body space can proceed undisturbed.

The oversize of the tubular body transverse to the slit can be produced by the tubular body having the correct size in this direction but the valve chamber being undersized. This has the advantage that a duckbill valve of standard construction may be used. On the other hand, the valve can be provided oversized and the valve chamber in the correct size, which offers the advantage of, for instance, being able to retrofit it to existing standard trocar sleeves.

Accordingly, the term "oversized" as used herein is meant to indicate the condition wherein the tubular body is larger, in a width dimension, that the corresponding portion of the valve chamber such that the tubular body must be compressed to be inserted into the valve chamber. In one instance, the tubular body is circular and is to be inserted into an oval valve chamber. When at rest or uninstalled, the tubular body has a diameter that is larger than the short side of the oval valve chamber. Accordingly, the tubular body must be compressed to fit within the short side of the valve chamber, and compression of the tubular body takes place in a direction essentially transverse to the slit. Alternatively, the tubular body, at rest, is oval-shaped and the valve chamber is circular. In this case, the slit in the tubular body traverses the short side of the oval tubular body. Since the long side of the tubular body is longer than the circular valve chamber, in order to fit within the valve chamber, the long side of the tubular body must be compressed. In either case, the tubular body has an at-rest or uninstalled size dimension, in a direction transverse to the length of the slit, of a first value and the valve chamber has a size dimension of a second value. The first value is larger than the second value such that, during installation, compression of the tubular body takes place essentially transverse to the length of the slit.

Since valve chambers commonly have circular internal cross-sectional shapes, it is recommended that the oversize be created by a slight oval deviation from the circular standard cross-sectional shape but attention should be paid to the correct angular positioning of the oval shape with respect to the direction of the slit in order to produce the desired compression of the duckbill valve transverse to the slit.

In further accordance with the present invention a standard trocar sleeve with a circular internal cross-sectional shape of the valve chamber can be used. The exact positioning of the oversize transverse to the slit is produced during manufacture of the duckbill valve. When inserting the duckbill valve into the- valve chamber no attention need be paid to the angular position so that installation is simplified.

BRIEF DESCRIPTION OF THE DRAWINGS

The invention is illustrated schematically by way of example of the drawings, in which.

DETAILED DESCRIPTION OF THE PREFERRED EMBODIMENT

Figure 1:
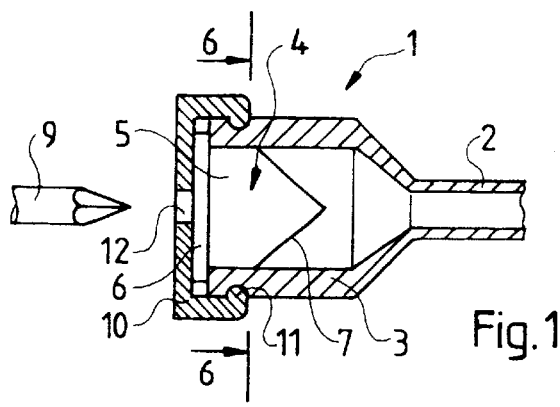
FIG. 1 is an axial sectional view of a trocar sleeve in accordance with the invention with a duckbill valve inserted.
Figure 2:
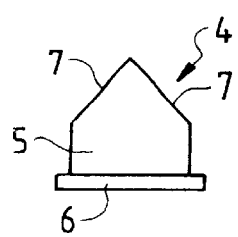
FIG. 2 is a side view of the duckbill valve shown in FIG. 1 in the direction of the slit.
Figure 3:
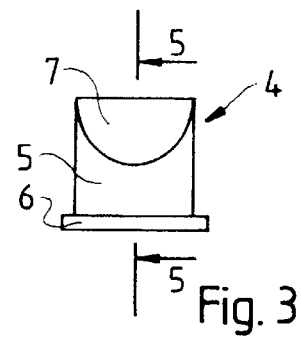
FIG. 3 is a side view corresponding to FIG. 2, but perpendicular to the slit.
Figure 4:
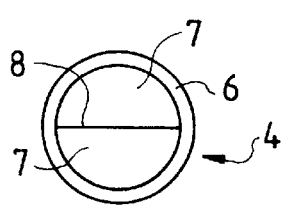
FIG. 4 is an axial view of the duckbill valve shown in FIGS. 1–3.
Figure 5:
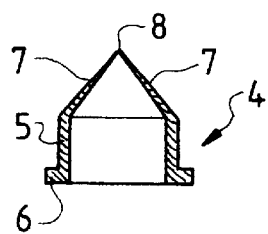
FIG. 5 is a sectional view on the line 5—5 in FIG. 3.

FIG. 1 shows a trocar sleeve 1 with an insertion tube 2, which is to be positioned in the stomach space of a patient, e.g. through a perforation in the stomach wall. Disposed at the proximal end of the insertion tube 2 is a valve chamber 3, inserted into the substantially cylindrical portion of which there is a duckbill valve 4, which is shown in FIGS. 2 to 5 in the uninstalled state.

The duckbill valve 4 has a tubular body 5, which carries an external flange 6 at one end. The tubular body 5 is of tapered construction in the manner of a pitched roof at the other end with two oblique walls 7. A slit 8 extends in the ridge transverse to the axis of the tubular body 5. If, as shown in FIG. 1, an instrument 9 (a trocar pin in the exemplary embodiment) is inserted from the exterior through the valve chamber 3 and the insertion tube 2 insrument, moves in the interior of the duckbill valve 4 against te oblique walls 7, pushes them aside and thus opens the slit 8 in order to be able to pass through it. When the instrument 9 is withdrawn, the slit 8 of the duckbill valve 4, which consists of elastic material, recloses.

If the body space in which the insertion tube 2 of the trocar sleeve 1 is positioned, is under gas pressure, the gas pressure acts through the insertion tube 2 in the interior of the valve chamber 3 on the oblique walls 7, which are acted on by the ambient atmosphere on the other side. Closing forces resultant obliquely to the axis on the oblique walls 7 are produced which close the slit 8 in a gas tight manner. The valve 4 thus acts as a non-return valve in a manner similar to a non-return flap.

As shown in FIG.1, an apertured diaphragm 10 is provided which consists of elastic material and is retained in the axial direction with an internal flange 11 on an external groove on the valve chamber 3. It extends over the external flange 6 on the duckbill valve 4 and holds it securely in the valve chamber 3 against internally acting pressure forces. Provided in the apertured diaphragm 10 coaxally with the insertion tube 2 is a hole 12 with a diameter matching the shaft of the instrument 9 in order to form an elastic seal with it to prevent the discharge of gas when the duckbill valve 4 is open.

If the duckbill valve 4 is in the closed position illustrated in FIG. 1 without an instrument inserted in it, its sealing action is dependent on the elastic restoring forces of the material of which the duckbill valve 4 consists. Only when relatively large gas forces act on the duckbill valve from the interior are closure forces through the oblique wall 7 added. At low pressures, however, leaks can occur, particularly with imprecise manufacture of the slit 8.

Figure 6:
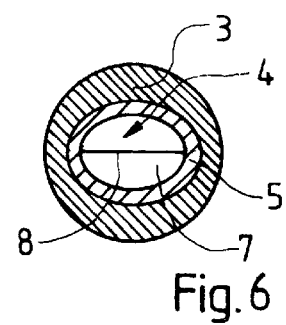
FIG. 6 is a sectional view on the line 6—6 in FIG. 1.

In order to prevent this, the cross-section of the valve chamber 3 is of oval shape, as may be seen in FIG. 6, while using a standard duckbill valve 4 with a circular external shape of the tubular body 5, specifically with the smaller diameter in the direction transverse to the slit 8.

If the duckbill valve is inserted into the valve chamber 3 in the appropriate angular orientation, its tubular body 5 is compressed inwardly in the direction transverse to the slit 8. An additional, pre-stressing closing force is thus exerted on the slit 8 which holds it cleanly closed, even in the unpressurised state.

The appropriate angular orientation of the circular tubular body 5 with respect to the internally oval valve chamber 3 can be assisted by means which ensure the precise angular position during insertion, such as markings on the duckbill valve 4 and the valve chamber 3 or e.g. by tongue and groove engagement for angularly locked form locking engagement.

Figure 7:
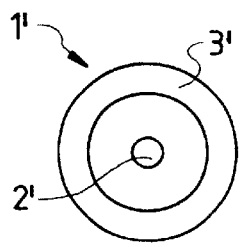
FIG. 7 is an axial view of a second embodiment of the trocar sleeve on the opening of the valve chamber and FIG. 8 is an axial view corresponding to FIG. 4 of a duckbill valve with an oval external cross-section.
Figure 8:
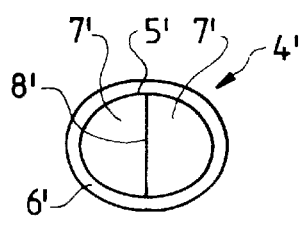

FIGS. 7 and 8 show a second embodiment of the trocar sleeve which substantially corresponds to the embodiment described above. The same reference numerals, provided with a dash, are used.

The difference of this embodiment with respect to the embodiment described above is that in this case the internal cross-sectional shape of the valve chamber 3' is circular but the duckbill valve 4' is prefabricated with an oval external cross-sectional shape of the tubular body 5'. The larger diameter extends transverse to the slit 8'. When the oval duckbill 4' is inserted into the circular valve chamber 3', it is compressed in the direction transverse to the slit 8' with the same effect as in the first embodiment described above.

In all the described embodiments, care should be taken when manufacturing the components that the external periphery of the tubular body 5,5' corresponds to the internal periphery of the valve chamber 3,3', at least with regard to all but relatively small manufacturing tolerances, so that the tubular body 5,5' can be inserted easily, but fittingly, and without any large compression, except the desired deformation transverse to the slit 8,8'.

In the second embodiment of FIGS. 7 and 8, no attention need to paid to the angular orientation during insertion.

The valve chamber and the tubular body of the duckbill valve are illustrated in the Figures with round and slightly oval cross-sectional shapes, respectively. Other, e.g. rectangular, cross-sectional shapes can, however, also be provided in which a gentle compression of the slit is effected as a result of an oversize or undersize, corresponding to the conditions in the described embodiments. The compression of the tubular body in the direction transverse to the slit can also be achieved in further embodiments, for instance, by projections on the inner surface of the valve chamber or similar constructional features.

What is claimed is:

1. A combination trocar sleeve (1, 1') and valve for introducing instruments (9) into gas filled body spaces, said sleeve including an insertion tube (2, 2') and a valve chamber (3, 3') proximally arranged thereon with a duckbill valve (4, 4') of elastic material disposed therein, said duckbill valve comprising a tubular body (5, 5') that extends coaxially with respect to an axis of the insertion tube, said tubular body having, at its end directed toward the insertion tube (2, 2'), two flat oblique walls (7, 7') that form a ridge with a slit (8, 8') extending transverse to the tube axis, and wherein the tubular body (5, 5'), when uninstalled, has a size dimension in a direction transverse to the slit (8,8'), said size dimension being a first value, and wherein said internal valve chamber (3, 3'), which is adapted to receive said tubular body, has a size dimension of a second value, said first value being greater than said second value.

2. The combination trocar sleeve and valve as claimed in claim 1, wherein the valve chamber (3') has a circular internal cross-sectional shape and the tubular body (5') has an oval external cross-sectional shape, a largest diameter of said oval external shape extending transverse to the slit (8') and being larger than an internal diameter of the valve chamber (3').

3. The combination trocar sleeve and valve as claimed in claim 1, wherein an internal periphery of the valve chamber (3, 3') is substantially equal to an external periphery of the tubular body (5, 5').

* * * * *

UNITED STATES PATENT AND TRADEMARK OFFICE
CERTIFICATE OF CORRECTION

PATENT NO. : 6,439,541 B1
DATED : August 27, 2002
INVENTOR(S) : Nosel et al.

It is certified that error appears in the above-identified patent and that said Letters Patent is hereby corrected as shown below:

<u>Title page,</u>
Item [57], ABSTRACT,
Line 4, delete "duck bill value" and insert -- duckbill valve --.

<u>Column 1,</u>
Line 13, after "like" insert -- , -- (comma).
Line 20, delete "The".
Line 35, delete "if for example the" and insert -- if, for example, the --.
Line 52, after "sleeve" insert -- , -- (comma).
Line 53, after "seal" delete -- , -- (comma).

<u>Column 2,</u>
Line 35, delete "the-" and insert -- the --.

<u>Column 3,</u>
Line 8, after "2" insert -- , -- (comma).
Line 9, delete "instrument,".
Line 10, delete "te" and insert -- the --.
Line 10, after "7" insert -- instrument 9 --.

Signed and Sealed this

Fifteenth Day of October, 2002

*Attest:*

*Attesting Officer*

JAMES E. ROGAN
*Director of the United States Patent and Trademark Office*